United States Patent [19]

Clark

[11] 4,057,055

[45] Nov. 8, 1977

[54] TOENAIL APPLIANCE AND METHOD

[76] Inventor: John H. Clark, 104 Biltmore Ave., Wheeling, W. Va. 26003

[21] Appl. No.: 607,050

[22] Filed: Aug. 22, 1975

[51] Int. Cl.² .............................................. A61F 5/00
[52] U.S. Cl. ................................................. 128/81 A
[58] Field of Search ........................... 128/81 A, 81 R

[56] References Cited

U.S. PATENT DOCUMENTS

| | | | |
|---|---|---|---|
| 884,376 | 4/1908 | Foster | 128/81 A |
| 1,708,716 | 4/1929 | Andersen | 128/81 A |
| 1,785,376 | 12/1930 | Buckner | 128/81 A |
| 2,499,851 | 3/1950 | Cronholm | 128/81 A |
| 2,505,086 | 4/1950 | Andrews | 128/81 A |
| 2,746,451 | 5/1956 | Parker | 128/81 A |
| 3,032,032 | 5/1962 | Gifford | 128/81 A |

*Primary Examiner*—John D. Yasko
*Attorney, Agent, or Firm*—Fay & Sharpe

[57] ABSTRACT

Method and apparatus for reshaping an incurvated or distorted toenail for the purpose of alleviating conditions incident to the development of an ingrown toenail. The appliance and method provide for the straightening of the toenail through the application of an external force system to the nail surface producing the result that the lateral margins of the nail are caused to be removed and lifted from the soft tissues of the nail groove. The appliance consists of a pair of post members adhesively secured to the surface of the nail and one or more tensioned elastomeric members secured to the post members in a manner to cause a lifting and straightening force to be exerted on the nail.

17 Claims, 17 Drawing Figures

TOENAIL APPLIANCE AND METHOD

BACKGROUND OF THE INVENTION

This invention relates to method and apparatus for reshaping and straightening an incurvated toenail or a deformed toenail that has become ingrown.

An ingrown toenail is one in which one or both lateral margins of the nail become embedded in the soft tissues of the nail groove thus producing inflammation. The edge of the nail digs into the soft tissues and forms a saw-tooth cutting edge, which produces a callus, warty growth, fissure and infection.

There are many causes attributed to ingrown toenails including short and pointed shoes, high heels, short or tight stockings, improper trimming of the nails, and deformation of the nail such as is the case with an incurvated nail.

Surgical procedures with respect to ingrown toenails may take several different forms depending upon the severity of the condition, the degree of infection, etc. A partial procedure may be performed in which an incision is made in the toe, under local anesthesia, in order to excise a part of the nail and the entire inflamed area of the skin. In severe cases a radical procedure or complete removal of the nail is called for.

When a toenail shows a tendency to dig into the skin margin it has been known, in the prior art, to compel growth of the nail above the margin by inserting under the edge of the nail a wedge or other means (such as a blunt toothpick) in order to lift the nail. Alternately, it has been known to exert a force on the nail by positioning a hook under the nail by and thereafter applying a force to the hook in order to lift the nail.

The application of such prior art devices as wedges and hooks to the toenail in order to attempt to redirect the growth of the nail is, by necessity, quite painful to the patient. In most cases the patient doesn't recognize the need for treatment until such time as the lateral margins of the nail have started to embed themselves in the soft tissues of the nail groove producing inflammation. Therefore, the ability of the patient or the patient's doctor to redirect the growth of the nail at such time as the toe has become inflamed is somewhat limited without the patient encountering great pain.

This invention provides for apparatus and method for straightening or reshaping an incurvated nail through the application of an external force system to the nail in a manner that does not require the painful application of either a wedge or a hook to the nail in order to redirect the growth thereof. This invention makes it possible to apply an external force system to the nail either before or at such time as the toe of the patient has become tender and without the pain normally associated with apparatus and methods known to the prior art.

BRIEF DESCRIPTION OF THE INVENTION

Briefly described the method and apparatus of this invention provide for the application of an external force system to an incurvated nail for the purpose of redirecting or reshaping the growth thereof in order to alleviate the growth condition known as an ingrown toenail. The apparatus of this invention is comprised of a pair of spaced apart post members that are caused to be adhered to the surface of the nail generally along the lateral margins thereof. One or more tensioned elastomeric members are secured to the post members so as to impart a compressive force to the nail causing the lateral margins thereof to be lifted from the soft tissues of the nail groove. The appliance is designed to be retained in use at the surface of the nail for so long a time as is necessary in order to achieve a straightening of the nail and an elimination of pain associated with an ingrown toenail.

The method of this invention is directed to method steps for placing a toenail in a state of compression through the application of a tensile force to portions of the nail surface providing for a lifting force which tends to straighten the nail and remove the edges thereof from deep contact with the nail groove.

DESCRIPTION OF THE DRAWINGS

A more complete description of the apparatus and method of this invention will now be made with reference to the accompanying drawings in which.

DESCRIPTION OF THE PREFERRED EMBODIMENT

Figure 1:
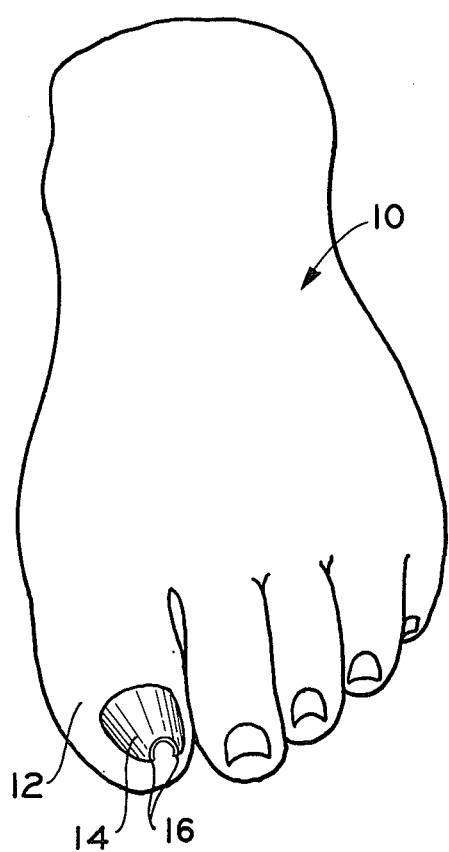
FIG. 1 is an elevational view of a portion of the foot and showing an incurvated toenail in the large toe of the foot.

Reference will first be made to FIG. 1 wherein there is shown a portion of a human foot 10 including a large toe 12 with a deformed or incurvated toenail 14. As will be observed from examination of the nail 14 of FIG. 1, the curvature of the nail is such that the extreme corners 16 are closely spaced.

The condition of the nail as shown in FIG. 1 may be brought about by many factors including heredity, style of shoes worn by the patient, stockings worn by the patient, to name a few. This condition may or may not be troublesome to the patient depending upon whether the nail has started to embed itself in the soft tissues of the nail groove producing inflammation. It has been found, however, than an extremely incurvated nail of the type illustrated in FIG. 1 is susceptible to problems associated with ingrown toenails since the edges of the nail are growing in a manner that could result in the nail becoming embedded in tissues of the nail groove.

The apparatus and method of this invention is particularly directed into incurvated nails of the type shown in FIG. 1.

Figure 2:
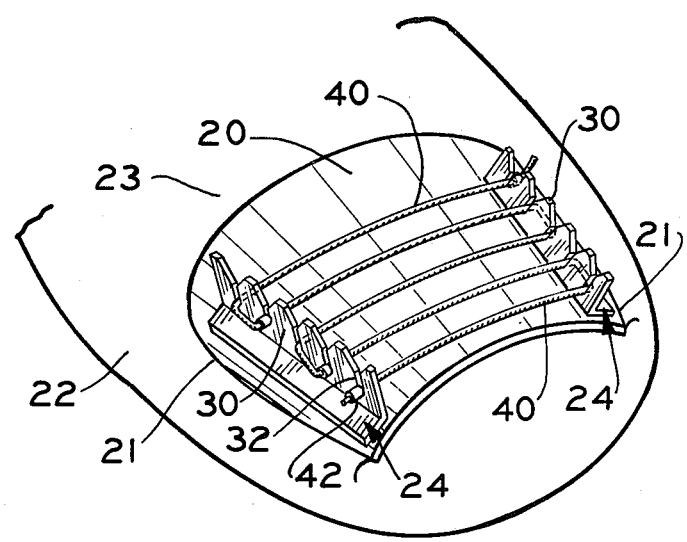
FIG. 2 is an elevational view of a portion of the large toe of a human foot in which the preferred embodiment of the apparatus of this invention has been installed at the nail surface.
Figure 4:
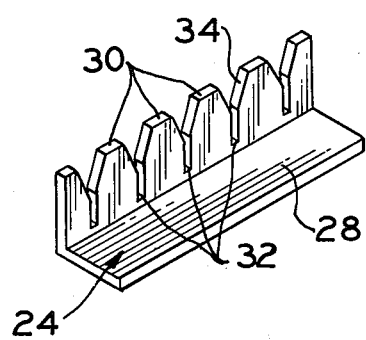
FIG. 4 is an elevational view showing a post member of the preferred embodiment of the apparatus of this invention.

Turning now to FIG. 2 the preferred embodiment of the apparatus of this invention is shown installed in place on the exterior surface of the nail 20 of the large toe 22. The preferred form of applicant's apparatus includes a pair of post members 24 secured to the external surface of the nail by means of adhesive. In FIG. 4 it will be noted that post member 24 is generally L-shaped in section and includes a bottom planar portion 28 and an upstanding portion defined by a series of projections 30 separated by a number of grooves 32. Grooves 32 project outwardly or diverge at 34 in order to facilitate installation of the tensioned elastomeric member as will be described more fully hereafter.

Post member 24 is adapted to be applied to the external surface of nail 20 of FIG. 2 by means of the application of a suitable adhesive to the bottom surface of the planar portion 28. Any suitable bonding material may be utilized known to those skilled in the art such as epoxy, rubber based elastomeric, or cyanoacrylate adhesive materials. Applicant has found that a fast polymerizing cyanoacrylate adhesive has performed well in tests and may be readily applied by a user.

After application of an adhesive to the post member 24 it is caused to be secured to the external surface of the nail preferably along the lateral edge thereof in the manner shown in FIG. 2. As will be observed the post member 24 has a length approximating the length of the lateral edge of the nail 20 in order that an external force may be applied to the entire lateral edge of the nail.

In the preferred embodiment of FIG. 2 a pair of spaced apart post members 24 are installed at the nail surface, preferably each post member being located along a respective lateral edge 21 of the nail.

Figure 5:
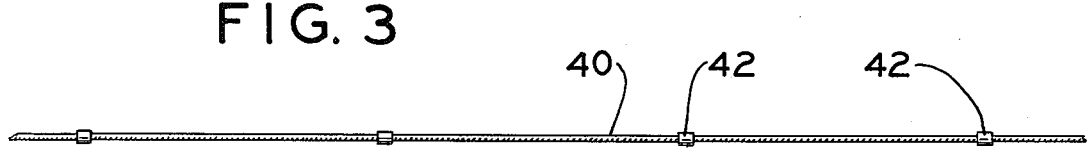
FIG. 5 is an elevational view of a portion of the elastomeric member of the preferred embodiment of the apparatus of this invention.

After the post members have been secured to the nail surface, a tensioned elastomeric member 40 is, in the preferred embodiment, laced throughout the post members in the manner shown in FIG. 2. The diverging grooves 32 facilitate installation of the member 40. As shown in FIG. 5 the elastomeric member 40 is provided with a plurality of nodes 42 approximately every quarter inch along the length of the member. Nodes 42 cooperate with projections 30 of the post members 24 to facilitate retention of the elastomeric member as the appliance is installed.

In the preferred embodiment the elastomeric member 40 is made from clear natural rubber having a diameter of approximately 0.030 inches or plastic having a diameter of approximately 0.020 inches.

Threading of the elastomeric member 40 through the post members 24 is achieved by causing a node 42 to be received within a groove 32 at one end of the post member as is shown in FIG. 2 and thereafter causing the elastomeric member to be passed throughout opposed grooves defined by the respective post members 24. A plurality of strands of elastomeric material may be laced throughout the post members as shown in FIG. 2 or, alternately, additional lacing of elastomeric material may be made as a double pass can be facilitated by the relatively deep grooves 32 of the post members. While the lacing of FIG. 2 is generally of a parallel nature it can be appreciated that diagonal lacing may be imparted to the post members or, alternately, a combination of parallel and diagonal lacing may be used as required.

Figure 3:
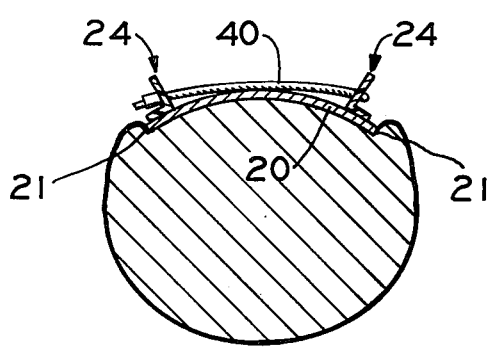
FIG. 3 is an elevational cross-sectional view of the large toe of FIG. 2 in which the preferred embodiment of the apparatus of this invention has been installed.

A cross-sectional view of applicant's apparatus as installed at the surface of the large toenail is shown in FIG. 3. It will be appreciated from a study of FIG. 3 that while the elastomeric member 40 is in a state of tension as it is wound or laced through the respective post members 24 the net effect of applicant's apparatus is to place the nail 20 in a state of compression thus promoting a straightening of the nail 20 and a lifting of the lateral edges 21 of the nail out of the soft tissue of the toe thus preventing a deep embedding of the lateral edges into such tissue.

While in the preferred embodiment of FIG. 2 the post members 24 are shown positioned essentially parallel to the lateral edges 21 of the nail it should be appreciated that variations in the position of the post members may be practiced depending upon the extent of deformation of the nail.

Figure 6:
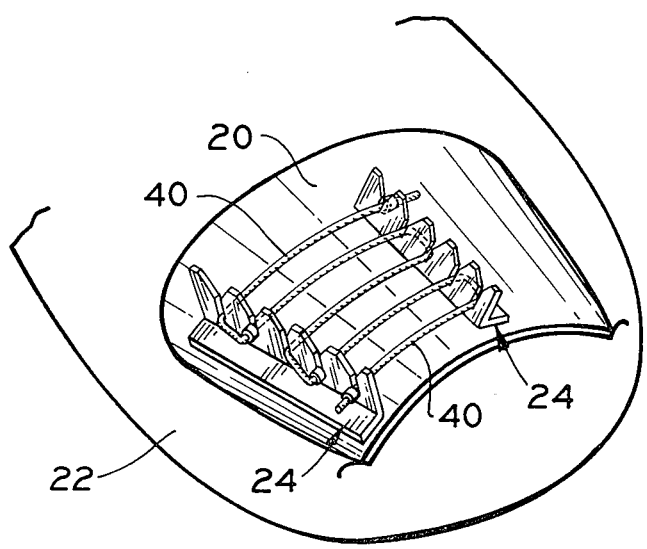
FIG. 6 is an elevational view of a portion of the large toe of a human foot similar to FIG. 2 in which the preferred embodiment of the apparatus of this invention has been installed at the nail surface in a manner differing from that shown in FIG. 2.

Thus in some instances it may be deemed desirable to position one of the post members at approximately the midportion of the nail 20 as shown in FIG. 6 while positioning the other of the post members near one of the lateral edges thereof. In this manner straightening of one of the lateral edges of the nail may be achieved. By reversing the application of the post members the other lateral edge of the nail may similarly be straightened.

The post members 24 may be fabricated from any suitable material. In the preferred embodiment a copolymer material (specifically injection molded nylon) is used.

In the preferred embodiment the post members are approximately 0.100 inches high and 0.500 inches long. Applicant's appliance, therefore, does not produce an appreciable protrusion from the toe and thus may be worn with many types of footwear without discomfort to the user. Obviously the height and length of the appliance may be varied to meet individual requirements.

It will be noted that in the preferred embodiment of FIG. 2 the post members 24 are of such a length that essentially the entire length of the nail is acted upon by the external application of the force system. Thus virtually the entire nail is straightened by the applicance of this invention not just the distal end thereof. With suitably long post members applicant's apparatus may direct a straightening force into the nail root under the nail fold 23 thus affording a greater opportunity to straighten the entire nail.

It will be apparent from a study of FIG. 2 that varying degrees of tension may be applied to the nail post members depending upon several factors including the degree of flexibility of the post material, the Shore durometer value of the elastomeric material, the degree of elongation of the elastomeric material and the degree of flexibility of the nail itself. It is conceivable, therefore, that a weak nail or a nail exhibiting a high degree of flexibility could possibly be overcompressed. Such a problem may be compensated for by the selection of a different elastomeric material or the application of less tension to the elastomeric material.

As has previously been pointed out, a feature of the appliance and method of this invention is the fact that the application of a force system to the nail is distributed over the entire nail for prolonged periods of time thus reducing extreme pressures at localized points. In this manner a controlled reshaping of the nail is achieved.

It has been noted above that while in the preferred embodiment of FIG. 2 both sides of the nail are simultaneously shaped it should be recognized that through the application of the post members to different locations on the nail surface one side of the nail may be shaped independently of the other (as shown in FIG. 6). It should further be recognized that while two post members are used in the preferred embodiment, additional post members could be utilized if desired. Indeed one or more additional post members could be positioned between the outwardly positioned post members and various lacing arrangements of the elastomeric material may be employed.

While in the preferred embodiment of FIG. 2, generally elongated post members are secured to the nail surface it should be appreciated that shorter or longer post members may be used depending upon the condition of the nail being treated.

MODIFICATIONS OF THE INVENTION

Figure 7:
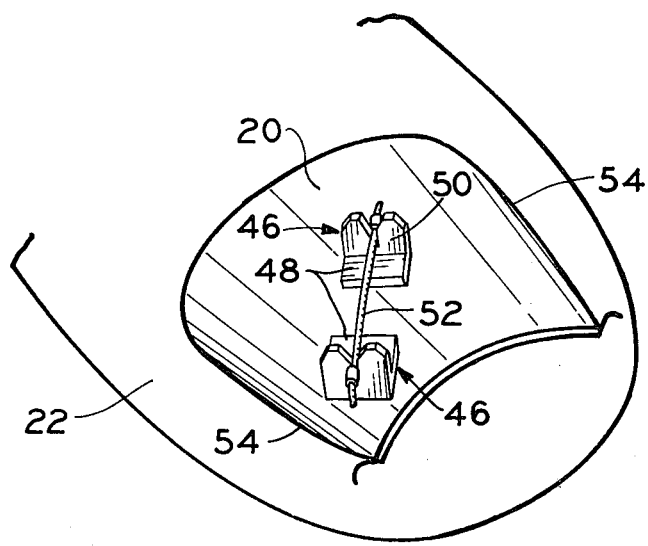
FIG. 7 is an elevational view of a portion of the large toe of the human foot similar to that shown in FIG. 2 but with a modified form of the apparatus of this invention installed at the nail surface.

A modification of the preferred embodiment of applicant's apparatus is shown in FIG. 7 wherein a pair of relatively short post members 46 are adhesively secured to the exterior surface of nail 20. Post members 46 are similar to post members 24 previously described although the bottom planar portions 48 thereof define considerably less area than corresponding portions 28 of post members 24. Similarly the projections 50 of post members 46 are considerably less in number than like projections 30 of post members 24. In fact only a single groove is defined in the post members 46 of the modification of the preferred embodiment as shown in FIG. 7 in order to receive the elastomeric material 52 as shown.

FIG. 7 also shows a further variation in the preferred embodiment of this invention as the post members are not positioned generally parallel to the lateral edges of the nail. Rather post members 46 of FIG. 7 are positioned at an angle with respect to the lateral edges 54 of nail 20 in order to direct a force system to the external surface of the nail for the purpose of alleviating a particularly distorted condition existing at only a portion of the nail.

It will be appreciated from a study of FIGS. 2, 6 and 7, therefore, that the appliance of this invention makes it possible to direct a force system to the nail at virtually any desired location in order to alleviate conditions incident to an incurvated or distorted nail no matter what the orientation of the nail or the degree of distortion thereof.

Further modifications to the preferred embodiment of the apparatus of this invention are shown in FIGS. 10-15.

Figure 11:
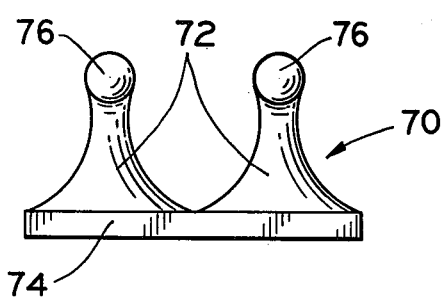
FIG. 11 is an elevational lengthwise view of the modified post member as shown in FIG. 10.
Figure 10:
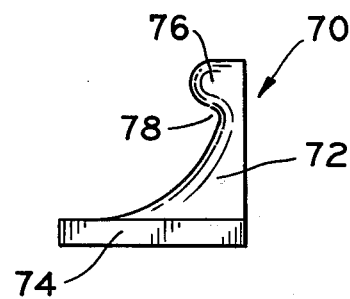
FIG. 10 is an elevational side view of a modification of the post member of this invention.

In FIGS. 10 and 11 there is shown a modification of applicant's post member. Post member 70 of FIG. 11 is generally defined by a plurality of upstanding portions 72, a base 74, and protuberances 76. Protuberances 76 defined tension member receiving areas 78 (FIG. 10) in order to facilitate the securing of a tension member to the post member. The modified embodiment of the post member as shown in FIGS. 10 and 11 is adapted to be applied to the surface of the nail in generally the same manner as the post members 24 as shown in FIG. 2. That is to say, a suitable adhesive is applied to the bottom surface of the base 74 and the post members are thereafter secured to the surface of the nail.

Figure 12:
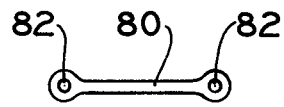
FIG. 12 is an elevational view of a modified form of tension member of this invention.

In FIG. 12 there is shown a modification of the tension member of applicant's apparatus. The tension member of FIG. 12 is defined by an elastomeric link 80 having expanded ends in which are defined apertures 82. The tension member of FIG. 12 is adapted to be applied to the post members by positioning the link such that the upstanding portions of the post members are received in the apertures 82. Obviously a plurality of links may be used with each appliance depending upon the degree to which it is desired to apply an external force system to the nail.

Figure 13:
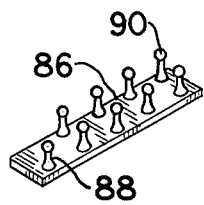
FIG. 13 is an elevational view of a further modified form of post member of this invention.

In FIG. 13 there is shown a further modification of applicant's post member. The structure of FIG. 13 includes a base 86 and a plurality of upstanding fingers 88. As will be noted from a study of FIG. 13 each finger 88 has a bulbous end 90 which facilitates the securing of a tension member to the post member.

Figure 14:
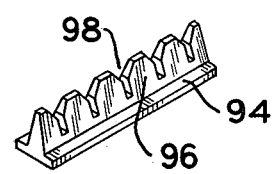
FIG. 14 is an elevational view of a still further modification of post member of this invention.

In FIG. 14 there is shown a still further modification of applicant's post member. The structure of FIG. 14 includes a base 94 and a generally centrally located ridge member 96 which is interrupted periodically by grooves 98 thus to define a plurality of upstanding members about which a tension member may be secured.

The modified embodiments as shown in FIGS. 13 and 14 are adapted to be secured to the surface of the nail by applying suitable adhesive to the bottom surface of the respective bases 86, 94.

It will be appreciated from a study of FIGS. 10-14 that many modifications to the post member are possible within the spirit of this invention in order to achieve applicant's objective which is to impart an external force system to the nail surface in order to provide for the straightening thereof.

Figure 15:
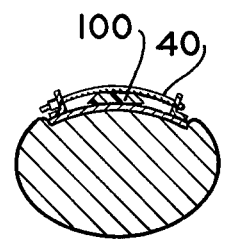
FIG. 15 is an elevational cross-sectional view of applicant's apparatus as applied to a toenail and in which the angle of action of the tension members is improved through the addition of a center member.

In FIG. 15 there is shown a modification in the installation of the apparatus of FIG. 2. More specifically it will be noted that in FIG. 15 a central member 100 is positioned at the surface of the nail in order to bias the elastomeric member 40 away from the nail surface thus to improve the angle of action of the elastomeric member with respect to the post members. As will be discussed further below it is desirable that the tension member be positioned at approximately 90° to the upstanding portion of the post member in order to achieve optimum application of an external force to the surface of the nail. The positioning of the central member 100 as shown in FIG. 15 improves the angle of action of the elastomeric member by causing the angle of intersection between the elastomeric member and the post ember to approach a desirable 90° value.

In tests conducted by applicant it has been found that the application of the appliance of this invention to an incurvated nail produced a dramatic straightening of the nail within several days after installation of the appliance. During the initial application period applicant's foot was soaked twice a day in hot water to which was added a commercial water softener. After initial straightening of a portion of the nail the applicance was removed and reinstalled at a different location on the nail surface. Applicant found that within several days the nail appeared normal and the appliance was removed.

Applicator

Figure 9:
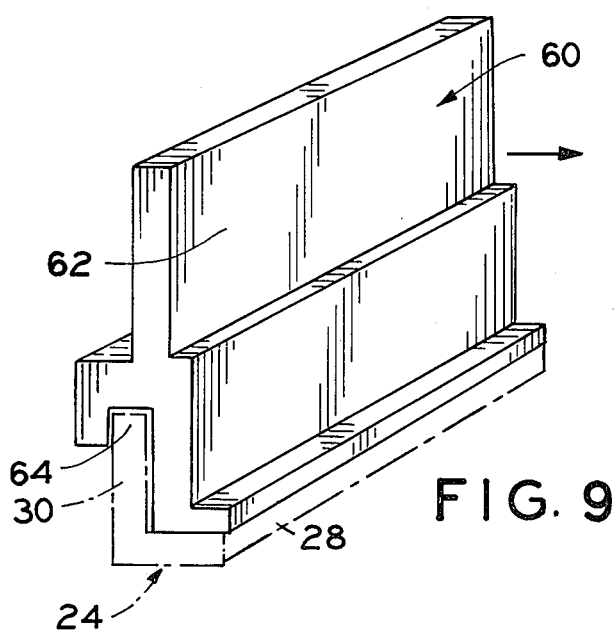
FIG. 9 is an elevational view of the applicator used for the installation of the post members of applicant's apparatus.

Because of the relatively small size of the post members it has been found desirable by applicant to provide an applicator of the type shown at 60 in FIG. 9. The applicator includes an essentially planar portion 62 adapted to be held by the person installing the appliance as well as a groove portion 64 adapted to receive the upstanding projections 30 of the post member 24. The applicator 60 is thus designed to be used for holding the post member while applying the adhesive to the planar portion 28 and also for retaining the post member in place at the nail surface while the adhesive is curing.

Force Diagram

Figure 8A:
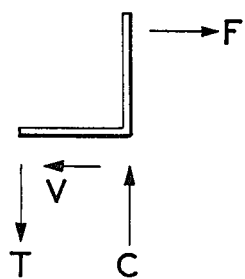
FIGS. 8(a), 8(b) and 8(c) are schematic representations of the forces applied to the toenail by applicant's apparatus and method.
Figure 8B:
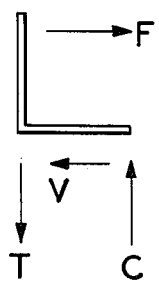
Figure 8C:
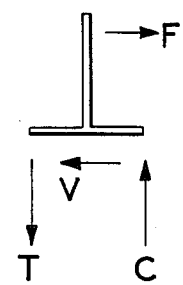

Schematic representations of the forces applied to the nail by the apparatus and method of this invention are shown in FIGS. 8(a), 8(b) and 8(c).

The force diagram as shown in FIG. 8(a) is achieved when a generally L-shaped post member is secured to the external surface of the nail in a manner similar to that shown in FIG. 2. That is to say, the schematic representation of FIG. 8(a) is achieved when the horizontal leg of the post member is positioned closest to the lateral edge of the nail.

The schematic representation of FIG. 8(b) is achieved by a reversal of the orientation of the post member from that shown in FIG. 2. That is to say, the force diagram of FIG. 8(b) is achieved when the vertical portion of the post member is positioned closest to the edge of the nail.

Finally, the schematic diagram as shown in FIG. 8(c) is achieved when apparatus such as that shown in FIG. 14 is used. That is to say, the diagram of FIG. 8(c) applies to post members of the type wherein the upstanding vertical portion of the post is positioned approximately midway on the base portion of the post.

The force F as shown in FIGS. 8(a), 8(b) and 8(c) represents the force applied to the post member by the elastomer or tension member. The force V represents the resisting shear force set up at the area of joinder of the post member and the surface of the nail. The forces T and C are couple forces. As will be appreciated, the force T (a tension force) is a lifting force applied to the surface of the nail. This is the straightening force applied to the nail.

In practice, the force F will act at various degrees to the vertical post member. In FIGS. 8(a), 8(b) and 8(c) the force F acts normal to the vertical post member there being established a 90° angle of intersection between the tensioned elastomeric member and the post member. It can be appreciated, however, that the force F may act at angles other than 90° with respect to the upstanding post member.

Referring to FIG. 8(a) it is assumed that the force F acts at an angle of 90° with respect to the vertical portion of the post member. It is further assumed that the length of the horizontal leg of the post member is equal to the length of the vertical leg of the post member. With these assumptions it may be computed that a force F of one pound as applied to the post member as shown in FIG. 8(a) will result in a force V of one pound and forces T and C of one pound each. That is to say, the application of a one pound force to the post member as shown in FIG. 8(a) will cause a one pound lifting force T to be applied to the surface of the nail.

A review of the three force systems as shown in FIGS. 8(a), 8(b) and 8(c) will show that the force system of FIG. 8(a) is superior to the force systems of FIGS. 8(b) and 8(c) insofar as the application of a lifting force to the nail. All three configurations, however, produce a couple (forces T and C) at the nail and, therefore, all three configurations may be used to achieve a straightening of the nail.

Method Described

The method of this invention for shaping an incurvated toenail comprises the steps of:

a. providing a first post member (24 FIG. 4) having a bottom planar portion 28 and an upstanding portion 30;

b. providing a second post member (24 FIG. 4) having a bottom portion 28 and an upstanding portion 30;

c. providing an elastomeric member 40;

d. adhesively securing said first post member to a portion of the surface of an incurvated toenail;

e. adhesively securing the second post member to the surface of such nail in spaced opposition to the first post member;

f. applying a tension force to the elastomeric member;

g. securing the tensioned elastomeric member to the first and second post members in order to create a couple at least a portion of the nail, the couple having a force which tends to straighten the nail.

Tests conducted by applicant have shown that upon application of the appliance and method of this invention a patient experiencing pain from an ingrown nail will obtain relief. It has been found by applicant that the appliance may be worn for as long a time as is necessary to reshape the nail without producing any discomfort to the user.

Applicant's appliance and method achieve relief from the pain and swelling associated with ingrown toenails. Applicant does not assert that his appliance or method is a permanent cure for the underlying causes of ingrown toenails. In some cases, however, the relief afforded by the appliance and method of this invention may be considered long term since a nail, once straightened, may not produce symptoms associated with an ingrown toenail for a considerable time.

What is claimed is:

1. An apparatus for straightening an incurvated toenail comprising:

a first post member adapted to be secured to only the external surface of such toenail, said first post member having a nail engaging portion and an upstanding portion;

a second post member adapted to be secured to only the external surface of such toenail in spaced opposition to said first post member;

a tension member under stress interconnecting said first post member and said second post member, said tension member being connected to said first post member at said upstanding portion, whereby, said upstanding portion of said first post member defines a moment arm extending from the surface of such toenail thereby establishing a couple at such toenail providing a rotating force tending to straighten such toenail.

2. The invention of claim 1 in which said upstanding portion of said first post member is defined by a plurality of generally vertical projections separated by grooves.

3. The invention of claim 2 in which said grooves diverge at the extremity of said projections.

4. The invention of claim 1 in which said tension member is defined by an elongated elastomeric member.

5. The invention of claim 4 in which said elastomeric member is defined by a plurality of spaced nodes.

6. The invention of claim 1 in which said first post member and said second post member are adapted to be secured to such toenail by means of an adhesive.

7. An appliance for an incurvated toenail comprising in combination:
- an elongated first post member defined by a bottom planar portion and a plurality of upstanding spaced apart generally vertical projections, the spaces between said projections defining grooves which taper outwardly;
- a second post member defined by a bottom planar portion and a plurality of upstanding spaced apart, generally vertical projections, the spaces between said projections defining grooves which taper outwardly;
- said first and second post member adapted to be adhesively secured to the surface of such nail at said planar portions;
- an elastomeric tension member interconnecting said first and second post members, said tension member being disposed in opposed grooves of said first and second post members; whereby,
- a couple is created at the nail surface, said couple defining a lifting force tending to straighten said nail and diminish the curvature thereof.

8. A method for shaping an incurvated toenoil comprising the steps of:
  a. providing a first post member having a bottom portion and an upstanding portion;
  b. providing a second post member having a bottom portion and an upstanding portion;
  c. providing an elastomeric tension member;
  d. adhesively securing said first post member directly to the external surface of such nail;
  e. adhesively securing said second post member directly to the external surface of such nail in spaced opposition to said first post member, said first and second post members being attached to only the external surface of such nail;
  f. elongating said elastomeric tension member;
  g. securing said elongated elastomeric member to said first and second post members; whereby,
  a couple is created at the nail surface, said couple defining a lifting force at said nail which tends to straighten said nail.

9. A method for shaping an incurvated toenail comprising the steps of:
  a. providing a first post member having a nail engaging portion and an upstanding portion;
  b. providing a second post member having a nail engaging portion;
  c. providing a tension member;
  d. adhesively securing said first post member to the external surface of such toenail;
  e. adhesively securing said second post member to the external surface of such toenail in spaced opposition to said first post member, said first and second post members being attached to only the external surface of such nail;
  f. attaching said tension member under stress to said first and second post members, said tension member being connected to said first post member at said upstanding postion; whereby,
  said upstanding portion of said first post member defines a moment arm extending from such toenail which establishes a couple thereby providing a rotational force at such toenail tending to straighten such toenail.

10. The method of claim 9 in which said first post member is adhesively secured to such toenail along the lateral edge of such toenail.

11. The method of claim 10 in which said second post member is adhesively secured to such toenail along the lateral edge of such toenail spaced apart from the lateral edge of such toenail adjacent said first post member.

12. An apparatus for straightening an incurvated toenail comprising:
- a first post member adapted to be directly secured to the external surface of such toenail, without any portion thereof positioned below the surface of such toenail, said first post member being defined by a toenail surface engaging portion and an upstanding portion, said upstanding portion being defined by at least one generally vertical projection;
- a second post member adapted to be directly secured to the external surface of such toenail without any portion thereof positioned below the surface of such toenail in spaced opposition to said first post member, said second post member being defined by a toenail surface engaging portion and an upstanding portion, said upstanding portion being defined by at least one generally vertical projection;
- at least one tension member under stress interconnecting said first post member and said second post member, said tension member adapted to be secured to said upstanding portions of said first and second post members; whereby,
- said upstanding portions of said first and second post members define moment arms extending from the surface of such toenail, there being provided at each post member a rotational force acting on such toenail tending to straighten such toenail.

13. The invention of claim 12 in which said first post member and said second post member have a length which approximates the length of the edges of the toenail to which said post members are adapted to be secured and said upstanding portions are defined by a plurality of generally vertical projections.

14. The invention of claim 13 in which said tension member is defined as an elastomeric member laced through opposed vertical projections of said post members.

15. The invention of claim 12 in which said tension member is defined as an elastomeric link having end portions which engage opposed vertical projections of said post members.

16. The invention of claim 12 in which said vertical projection is defined as a post member.

17. The invention of claim 16 in which said post member is defined by a bulbous end to facilitate attachment of said tension member.

* * * * *